United States Patent [19]

Lepage et al.

[11] Patent Number: 5,059,614
[45] Date of Patent: Oct. 22, 1991

[54] NOVEL ISOXAZOLE AND ISOXAZOLINE COMPOUNDS WITH ANTICONVULSANT ACTIVITY PROCESS FOR THEIR PREPARATION AND THERAPEUTIC COMPOSITION CONTAINING THEM

[75] Inventors: Francis Lepage, Creteil; Bernard Hublot, Paris, both of France

[73] Assignee: Novapharme, Paris, France

[21] Appl. No.: 443,133

[22] Filed: Nov. 29, 1989

[30] Foreign Application Priority Data

Nov. 30, 1988 [FR] France ................ 88 15718

[51] Int. Cl.$^5$ .................. A61K 31/42; C07D 260/04; C07D 261/10; C07D 261/20
[52] U.S. Cl. .................. 514/378; 514/379; 514/380; 548/240; 548/241; 548/243; 548/245; 548/246; 548/247; 548/248; 548/473; 560/358; 564/305; 568/716
[58] Field of Search .......... 548/245, 246, 247, 248, 548/240, 241, 243; 514/378, 380, 379

[56] References Cited

U.S. PATENT DOCUMENTS

| | | | |
|---|---|---|---|
| 2,126,329 | 8/1938 | Hoffer | 548/247 |
| 3,547,940 | 12/1970 | Brantley | 548/245 |
| 4,062,861 | 12/1977 | Yukinaga et al. | 548/241 |
| 4,322,429 | 3/1982 | Burow, Jr. | 548/245 |

FOREIGN PATENT DOCUMENTS

| | | | |
|---|---|---|---|
| 0048162 | 3/1982 | European Pat. Off. | |
| 2073284 | 10/1971 | France . | |
| 2106456 | 5/1972 | France . | |
| 2315923 | 1/1977 | France . | |
| 2084140 | 4/1982 | United Kingdom | 548/247 |

OTHER PUBLICATIONS

Paul et al., *Bull. Chim. Soc. Fr.*, pp. 140–142 (1963).

Bianchi et al., *Chemical Abstracts*, vol. 70, No. 47343 (1969).
Ammermann et al., *Chemical Abstracts*, vol. 96, No. 20085 (1982).

*Primary Examiner*—Cecilia Shen
*Assistant Examiner*—E. Bernhardt
*Attorney, Agent, or Firm*—Wegner, Cantor, Mueller & Player

[57] ABSTRACT

The object of the invention are anticonvulsant heterocyclic compounds of general formula:

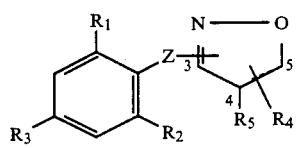

in which $R_1$ and $R_2$ is each selected from $C_1$–$C_4$ alkyl, phenyl, benzyl, trifluoromethyl or halogen, $R_3$ is selected from hydrogen, hydroxy, $C_1$–$C_4$ alkyl or alkoxy, $R_4$, in position 3 or 5, is selected from hydrogen, trifluoromethyl, $C_1$–$C_4$ alkoxy, $C_1$–$C_4$ alkyl, or $C_1$–$C_4$ hydroxyalkyl, $R_5$ is selected from hydrogen or $C_4$–$C_4$ alkyl or $R_4$ and $R_5$ together form a tetramethylene group, Z at position 3 or 5 on the heterocycle is selected from:

—N($R_6$)—CO—, —CO—N($R_6$)—,
—N($R_6$)—CO—N($R_6$)—

—CH($R_6$)—NH—CO—, or —NH—CO—CH($R_6$), in which $R_6$ is selected from hydrogen or $C_1$–$C_4$ alkyl.

17 Claims, No Drawings

NOVEL ISOXAZOLE AND ISOXAZOLINE COMPOUNDS WITH ANTICONVULSANT ACTIVITY PROCESS FOR THEIR PREPARATION AND THERAPEUTIC COMPOSITION CONTAINING THEM

The present invention relates, in a general manner, to novel heterocyclic derivatives endowed with anticonvulsant activity, a process for their preparation as well as therapeutic compositions containing them.

A relatively small number of agents having anticonvulsant activity is available. A large number of them exhibit disadvantages related to therapeutic escape phenomena, troublesome side effects such as diminution of vigilance, sleepiness, . . . or toxic effects, in particular hepatoxic effects.

The aim of the present invention is to provide novel compounds having anticonvulsant properties, and which are free from the disadvantages of the prior part.

Thus, the object of the present invention is heterocyclic compounds of general formula:

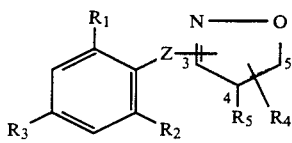

in which
$R_1$ and $R_2$ is each selected from $C_1$-$C_4$ alkyl, phenyl, benzyl, trifluormethyl or halogen, $R_3$ is selected from hydrogen, hydroxy, $C_1$-$C_4$ alkyl or alkoxy $R_4$, at position 3 or position 5, is selected from hydrogen, trifluoromethyl, $C_1$-$C_4$ alkoxy, $C_1$-$C_4$ alkyl or $C_1$-$C_4$ hydroxyalkyl, $R_5$ is selected from hydrogen or $C_1$-$C_4$ alkyl, or $R_4$ and $R_5$ together comprise a tetramethylene group, Z, at position 3 or 5 on the heterocycle, is selected from:

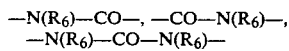

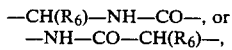

in which $R_6$ is selected from hydrogen or $C_1$-$C_4$ alkyl; the dotted line represents the possibility of a double bond, provided that, when Z is at position 5, $R_4$ and $R_5$ do not simultaneously represent hydrogen.

The preferred compounds (I) are particularly the isoxazoles.

Among the compounds of general formula I, those in which Z is —N($R_6$)—CO— in which $R_6$ is hydrogen are particularly preferred.

More particularly, examples of the preferred compounds according to the invention are:
3-(2,6-dimethyl phenylcarbamoyl) 5-methyl isoxazole
5-(2,6-dimethyl phenylcarbamoyl) 3-methyl isoxazole
3-(2,6-dimethyl phenylcarbamoyl) 5-hydroxymethyl isoxazole
3-(2,6-dimethyl phenylcarbamoyl) isoxazole
3-(2,4,6-dimethyl phenylcarbamoyl) 5-methyl isoxazole
3-(2-methyl 6-isopropyl phenylcarbamoyl) 5-methyl isoxazole
N-3-(5-methyl isoxazolyl) 2,6-dimethyl benzamide
3-(2-chloro 6-methyl phenylcarbamoyl) 5-methyl isoxazole
3-(2,6-dimethyl phenylcarbamoyl) 5-methyl isoxazoline These compounds are numbered 1, 16, 29, 6, 11, 14, 19, 13, 4, respectively, in the tables.

Another object of the present invention is a process for the preparation of the compounds of general formula I, wherein a compound of general formula:

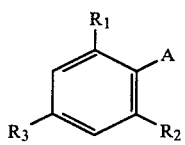

in which $R_1$, $R_2$, and $R_3$ are as defined in formula I and A is selected from —COOH, —COCl, —N($R_6$)H or —CH($R_6$)—NH$_2$ in which $R_6$ is selected from hydrogen, or $C_1$-$C_4$ alkyl, is reacted with a compound of general formula:

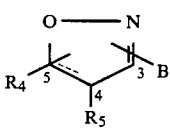

in which the symbols $R_4$ and $R_5$ are as defined in formula I and B at position 3 or position 5 on the heterocycle is selected from —COOH,—CH($R_6$)COOH,—COCl,—CH($R_6$)COCl, or —NR$_6$H in which $R_6$ is selected from hydrogen or $C_1$-$C_4$ alkyl and the dotted line represents the possibility of a double bond.

In particular,
a) when Z is selected from —N($R_6$)—CO—,—CH($R_6$)—NH—CO— or —NH—CO—CH($R_6$)—, $R_6$ being as defined in the general formula I, an amine of general formula II in which A is selected from —NR$_6$H or —CH($R_6$)—NH$_2$ is condensed with an acid or an acid chloride of general formula III in which B is selected from —COOH,—CH($R_6$)—COOH,—COCl or —CH($R_6$)COCl.

When an acid of general formula III is used, the reaction is carried out in the presence of dicyclohexylcarbodiimide (DCC) or carbonyldiimidazole (CDI) in a solvent which may be dimethylformamide (DMF) or tetrahydrofuran (THF) at a temperature between 10° and 25° C.

In the case in which an acid chloride (III) is used, the condensation is carried out in the presence of a proton acceptor such as triethylamine or potassium carbonate at a temperature between 20° and 120° C. in a neutral solvent such as toluene, acetone, etc.

b) When Z is -NR$_6$-CO-NR$_6$, an aniline compound of formula II in which A is NHR$_6$ is condensed with phosgene in order to form the corresponding isocyanate which is, in turn, condensed with an amine of formula III in which B is NR$_6$H, in a neutral solvent such as toluene, or THF at a temperature between 20° and 120° C.

c) When Z is —CO-N($R_6$)—, a compound of general formula II in which A is selected from —COOH or —COCl is condensed with a compound of general formula III in which B is —NR$_6$H. This reaction is carried out in the same manner as that in a) above.

The acids of general formula III are known in the literature.

In particular, the acids are:
isoxazole 3-carboxylic acid
isoxazole 3-carboxylic acid substituted at position 5 by methyl, ethyl, isopropyl, tert.butyl
4,5 dimethyl isoxazole 3-carboxylic acid
3-methyl isoxazole 5-carboxylic acid
4,5,6,7-tetrahydrobenzisoxazoline 3-carboxylic acid
5-methyl isoxazoline 3-carboxylic acid
4,5-dimethyl isoxazoline 3-carboxylic acid
5-methyl isoxazole 3-acetic acid
5-methoxy isoxazole 3-carboxylic acid The 5-trifluoromethyl isoxazole 3-carboxylic acid was prepared according to the standard procedure by condensation of trifluoroacetone and diethyloxalate, followed by condensation of the diketone formed with hydroxylamine.

The amines of general formula II are all commercially available products or are described in the literature, except in the case in which A is $CH(R_6)NH_2$, the synthesis of which was carried out by reduction of the corresponding ester by means of $LiAlH_4$, followed by substitution of the hydroxy by an amine function via the corresponding phthalimide.

d) When $R_4$ is $C_1$–$C_4$ hydroxyalkyl, it is also possible to condense a compound of general formula:

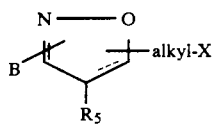

IV in which X is halogen, and B and $R_5$ are as defined in the formula III, with a compound of formula II.

These compounds are then treated with an alkali metal or silver carboxylate in order to form the corresponding acyloxyalkyl or benzoyloxyalkyl compounds (formula I: $R_4$=alkyl substituted by acyloxy or benzoyloxy). These latter are then hydrolyzed in the presence of a base or an acid in order to form the corresponding hydroxyalkyl compounds (formula I with $R_4$=hydroxyalkyl).

Some of the compounds of the invention possess one or more asymmetric carbon atoms. The corresponding optical isomers also form part of the invention.

The following examples illustrate the preparation of the compounds of formula I.

EXAMPLE 1:

Preparation of 3-(2,6-dimethyl phenylcarbamoyl) 5-methyl isoxazole (compound 1)

27 g (0.2 mole) of 2,6-dimethyl aniline are dissolved in 100 ml of toluene, 14.5 g (0.1 mole) of 5-methyl isoxazole 3-carboxylic acid chloride are added drop wise with stirring and the mixture is refluxed for 2h. The mixture is cooled and the hydrochloride formed is filtered off. The organic phase is washed with 10% sodium bicarbonate. After filtration and removal of the solvent, the product is recrystallized from cyclohexane or pentane. M.p.=100°. The yield is about 90%.

EXAMPLE 2

Preparation of 3-(2,6-dimethyl phenyl carbamoyl) 5-ethyl isoxazole (compound 2)

5.1 g (0.04 mole) of 5-ethyl isoxazole 3-carboxylic acid are dissolved in 100 ml of DMF under nitrogen, 13 g (0.08 mole) of carbonyl diimidazole are added and the mixture is stirred for 2 h at room temperature. 9.7 g (0.08 mole) of 2,6-dimethyl aniline are added and the mixture is stirred again for 48 h. After removal of the precipitate formed by filtration and evaporation of the solvent, the residue is crystallized from petroleum ether. M.p.=82°. The yield is 73%.

The compounds 3 to 26, 28, 31 are prepared by one or other of these methods (Ex. 1 or 2).

EXAMPLE 3

Preparation of N-(2,6-dimethyl phenyl)-N'-3-(5-methyl isoxazolyl) urea (compound 27)

a) Preparation of 2,6-dimethyl phenyl isocyanate 7 g (0.05 mole) of 2,6-dimethyl aniline dissolved in 20 ml of toluene are added dropwise to a 20% solution of phosgene in toluene (1.5 equivalents) maintained at 0° in an ice bath. The mixture is then heated at reflux for 3 h. The mixture is concentrated and the residue is distilled under vacuum. B.p.=100°/13 mm Hg. Yield: 76%.

b) Preparation of N-(2,6-dimethyl phenyl)-N'-(5-methyl 3-isoxazolyl) urea 7 g (0.04 mole) of the preceding isocyanate, 4 g (0.04 mole) of 3-amino 5-methyl isoxazole are heated at reflux for 16 h in a toluene THF mixture (100—100 ml). The precipitate formed is filtered off, the solution is concentrated. The crystals are recrystallized from an ethanol-water mixture. M.p.=200° Yield 64%.

EXAMPLE 4

Preparation of the compound 3-(2,6-dimethyl phenyl carbamoyl) 5-hydroxymethyl isoxazole (compound 29).

a) Preparation of 3-(2,6-dimethyl phenyl carbamoyl) 5-bromomethyl isoxazole 0.1 mole of 5-bromomethyl isoxazole 3-carbonyl chloride (J. C. Sircaretal, J. Org. Chem., 50 p 5723-27, 1985) is dissolved in 200 ml of toluene. 26 g (0.2 mole) of dimethyl aniline are added and the mixture is heated at reflux for 5 h. After concentration of the reaction mixture, the residue is washed with a carbonate solution. The oily residue is purified by passage through a column (Silica gel). F°=123°-124°.

b) Preparation of 3-(2,6-dimethyl phenyl carbamoyl) 5-acetoxymethyl isoxazole.

A mixture of 12.4 g (0.04 mole) of the bromomethyl compound previously prepared and 7.4 g (0.044 mole) of silver acetate in 100 ml of acetic acid is heated at reflux for 4 h. After cooling, the silver salt formed is filtered off and the solution is concentrated. The product is purified by passage through a column (silica gel).

c) Preparation of 3-(2,6-dimethyl phenyl carbamoyl) 5-hydroxymethyl isoxazole

The previously prepared acetoxymethyl derivative is dissolved in ethanol, 1.25 equivalents of a 10% sodium hydroxide solution are added and the mixture is heated at reflux for 30 min. After the usual work-up, the product is purified by passage through a column of silica (eluent $CH_2Cl_2$, then $CH_2Cl_2$-$CH_3OH$, 95-5). The yield is 40%. M.p.=95°.

The compound: No. 30 may be prepared in the same manner.

EXAMPLE 5

Preparation of the compound 3-(2,6-dimethyl benzyl carbamoyl) 5-methyl isoxazole (compound 28)

a) Preparation of 2,6-dimethyl benzyl alcohol 17 g of 2,6-dimethyl benzoic acid ethyl ester (0.095 mole) dissolved in 50 ml of ethyl ether are added dropwise as a function of the vigor of reflux to a suspension of 3.72 g (0.095 mole) of $LiAlH_4$ in 100 ml of ether. When the addition is complete, the mixture is heated at reflux for 2h and left to stand overnight. Excess hydride is decomposed by the gradual addition of water (while cooling the flask in an ice-water bath), then 10% HCl. After the usual work-up, the product is crystallized from petroleum ether. 10 g of product are obtained. M.p.=84°. Yield 77.5%.

b) Preparation of 2,6-dimethyl benzyl phthalimide 10 g (0.073 mole) of the preceding alcohol are dissolved in 300 ml of THF and 13.3 g (0.09 mole) of phthalimide are added followed by 22.9 g (0.087 mole) of triphenylphosphine and then 13.9 ml of diethylazodicarboxylate are added dropwise. The temperature rises to 45°. The mixture is then left to stand for 24h under nitrogen. The reaction mixture is concentrated and the residue is purified on a column of silica (eluent $CH_2Cl_2$). M.p.=154°. Yield: 92.7%.

c) Preparation of 2,6-dimethyl benzylamine 18 g (0.068 mole) of the phthalimido derivative, 13.5 g (0.27 mole) of hydrazine hydrate in 200 ml of ethanol are heated at reflux for 8 h. The solid obtained is filtered off, the solution is concentrated. After the usual work-up the residue is distilled. $B.p._{18\ mm}=125°-130°$. Yield: 66%.

d) Preparation of 3-(2,6-dimethyl benzyl carbamoyl) 5-methyl isoxazole

As in example 1, by replacing the 2,6-dimethyl aniline by the amine obtained in c) above.

The compounds of these examples as well as other compounds of formula I are presented in table II below.

The compounds according to the invention were shown to be endowed with interesting properties with respect to the nervous system, in particular with anti-convulsant properties likely to make them useful in the treatment of epilepsy or as supplements to anti-epileptic treatment, cerebral protection and memory enhancement.

Thus, the invention also includes the therapeutic compositions containing the compounds of general formula I as active ingredient.

Toxicological and pharmacological results demonstrating the properties of the compounds of formula I will be given below.

1. Pharmacological Activity

The anti-convulsant activity is measured by tests using electroshock and pentetrazol according to the method of A. SWINYARD (ADD PROGRAM OF NINCDS BY H. J. KUPFERBERG E. A. SWINYARD AND G. D. GLADDING in advances in epileptology/XIIth Epilepsy International Symposium edited by M. DAM, L. GRAM and J. K. PENRY-RAVEN press NEW-YORK 1981). The compounds are always administered (at 1/10th of the LD50) by IP injection into SWISS CD1 mice (Charles River) of 20-25 g mean weight. All of the substances are dissolved in a 0.9% sodium chloride solution or suspended in a 1% solution of carboxymethyl-cellulose or tween.

Electroshock test. Groups of 10 mice (1 control group and one treated group) are used for each compound. The treated group receives the test substance by the intraperitoneal route 30 mn before the electroshock. This is applied by means of corneal electrodes (50 milliamperes for 0.2 second). Protection is measured by the percentage of the animals not showing extension of the hind paws.

Pentetrazol seizures. 70 mg/kg of pentetrazol is injected s.c. into groups of 10 mice (1 control group and 1 treated group) in a volume of 0.2 ml/20 g body weight. The test substances are administered by the intraperitoneal route 30 mn before pentetrazol. The animals are observed for 30 mn. The number of chronic seizures lasting 5 seconds or longer is recorded as is the percentage of animals protected against chronic seizures.

The results are presented in the table below.

2. Cerebral Protective Activity 5 mice (20-25 g) receive an IP injection of the substance or the liquid vehicle 30 minutes before being placed in a closed chamber, where the atmospheric pressure is reduced to 210 mm Hg. The survival time (in seconds) is measured from the induction of hypoxia to the complete cessation of respiratory movements.

Compound one (50 mg/kg) prolongs the survival time significantly: +124%.

3. Determination of the lethal dose 50

The toxicity is measured by the technique of MILLER and TAINTER by the intraperitoneal route. The results are presented in the table below.

| Compound No. | IP Results in the mouse | | |
|---|---|---|---|
| | LD50 mg/kg | % protection against | |
| | | electroshock | Pentetrazol |
| 1 | 375 | 100 | 30 |
| 2 | 375 | 60 | 20 |
| 3 | 500 | 100 | 40 |
| 5 | 500 | 70 | 80 |
| 6 | 500 | 80 | 50 |
| 7 | 750 | 90 | 40 |
| 11 | 750 | 100 | 50 |
| 12 | 500 | 100 | 60 |
| 13 | 1000 | 100 | 50 |
| 14 | 2000 | 100 | 30 |
| 16 | 750 | 100 | 90 |
| 19 | 2000 | 100 | 30 |
| 23 | | 40 | 60 |
| 29 | | 100 | |

The therapeutic compositions according to the invention may be administered by the oral, parenteral or endorectal routes.

They are available in the form of tablets, sugar-coated pills, capsules, injectable solutions or suspensions and suppositories.

The amount of active ingredient administered obviously depends on the patient who is being treated, the route of administration and the severity of the disease.

However, the daily dosage is of the range of 10 to 300 mg.

The unit dose may be between 10 and 100 mg.

EXAMPLES OF FORMULATION

(1) Standard formula for tablets:
For 5000 20 mg tablets

| | |
|---|---|
| Compound of example 1 | 100 g |
| Microcrystalline cellulose | 1000 g |
| Sodium carboxymenthyl cellulose | 15 g |
| Magnesium stearate | 10 g |
| Total = | 1125 g |

Mix all of the constituents in a Turbula$^R$ mixer for 10 mn
Compress in an alternating machine, theoretical weight: 225 mg.

(2) Standard formula for capsules:
For 500 capsules, size 1, dosed at 10 mg

| | |
|---|---|
| Compound of example 1 | 50 g |
| Maize starch | 150 g |
| Lactose | 1250 g |
| PVP K30 | 75 g |
| Talc | 30 g |
| Magnesium stearate | 10 g |
| Total = | 1565 g |
| 50° alcohol = | QS |

Mix the following constituents for 10 min in a planetary mixer: Compound No. 1-maize starch-lactose-PVP.
Under continuous stirring slowly add the alcohol to give a satisfactory granulation.
Spread on trays, dry in an oven at 50° C.
Calibrate on an oscillating granulator, mesh size 1 mm
Mix the pellets with the talc and the magnesium stearate for 10 min in the Turbula$^R$.
Place in capsules, theoretical weight: 313 mg.

TABLE

| Compound No. | Z (position on the heterocycle) | $R_1$ | $R_2$ | $R_3$ | $R_4$ | $R_5$ | Hetero-cycle | F°C. |
|---|---|---|---|---|---|---|---|---|
| 1 | —NH—CO— (3) | $CH_3$ | $CH_3$ | H | 5-$CH_3$ | H | isoxazole | 100° |
| 2 | —NH—CO— (3) | CH3 | $CH_3$ | H | 5-$CH_2CH_3$ | H | isoxazole | 82° |
| 3 | —NH—CO— (3) | $CH_3$ | $CH_3$ | H | 5-$CH_3$ | $CH_3$ | isoxazoline | 60° |
| 4 | —NH—CO— (3) | $CH_3$ | $CH_3$ | H | 5-$CH_3$ | H | isoxazoline | 92° |
| 5 | —NH—CO— (3) | $CH_3$ | $CH_3$ | H | 5-$OCH_3$ | H | isoxazole | 139° |
| 6 | —NH—CO— (3) | $CH_3$ | $CH_3$ | H | H | H | isoxazole | 61° |
| 7 | —NH—CO— (3) | $CH_3$ | $CH_3$ | H | 5-$CH(CH_3)_2$ | H | isoxazole | 96° |
| 8 | —NH—CO— (3) | $CH_3$ | $CH_3$ | H | 5-$C(CH_3)_3$ | H | isoxazole | 166° |
| 9 | —NH—CO— (3) | $CH_3$ | $CH_3$ | H | 5-$CF_3$ | H | isoxazole | |
| 10 | —NH—CO— (3) | $CH_3$ | $CH_3$ | H | 5-$CH_3$ | $CH_3$ | isoxazole | 123° |
| 11 | —NH—CO— (3) | $CH_3$ | $CH_3$ | $CH_3$ | 5-$CH_3$ | H | isoxazole | 106° |
| 12 | $-\underset{\underset{(3)}{\mid}}{N}-CO-$ with $CH_3$ | $CH_3$ | $CH_3$ | H | 5-$CH_3$ | H | isoxazole | 120° |
| 13 | —NH—CO— (3) | $CH_3$ | Cl | H | 5-$CH_3$ | H | isoxazole | 84° |
| 14 | —NH—CO— (3) | $CH_3$ | $CH_3$—CH—$CH_3$ | H | 5-$CH_3$ | H | isoxazole | 112° |
| 15 | —NH—CO— (3) | $CH_3$—CH—$CH_3$ | $CH_3$—CH—$CH_3$ | H | 5-$CH_3$ | H | isoxazole | 161° |
| 16 | —NH—CO— (5) | $CH_3$ | $CH_3$ | H | 3-$CH_3$ | H | isoxazole | 120° |
| 17 | —NH—CO— (3) | $CH_3$ | $CH_3$ | H | —$(CH_2)_4$— | | isoxazoline | 80° |
| 18 | —NH—CO—$CH_2$— (3) | $CH_3$ | $CH_3$ | H | 5-$CH_3$ | H | isoxazoline | 124° |
| 19 | —CO—NH— (3) | $CH_3$ | $CH_3$ | H | 5-$CH_3$ | H | isoxazole | 180° |
| 20 | $-\underset{\underset{}{\mid}}{N}-CO-$ with $CH_2CH_3$ | $CH_3$ | $CH_3$ | H | 5-$CH_3$ | H | isoxazole | 72° |

TABLE-continued

| Compound No. | Z (position on the heterocycle) | R₁ | R₂ | R₃ | R₄ | R₅ | Hetero-cycle | F°C. |
|---|---|---|---|---|---|---|---|---|
| 21 | $\underset{(3)}{-\text{N}-\text{CO}-}$ with CH(CH₃)₂ on N | CH₃ | CH₃ | H | 5-CH₃ | H | isoxazole | 82° |
| 22 | —CO—NH— (5) | CH₃ | CH₃ | H | 3-CH₃ | H | isoxazole | 133° |
| 23 | —NH—CO— (5) | CH₃ | CH₃—CH—CH₃ | H | 3-CH₃ | H | isoxazole | 146° |
| 24 | $\underset{(3)}{-\text{N}-\text{CO}-}$ with CH₃ on N | CH₃ | CH₃—CH—CH₃ | H | 5-CH₃ | H | isoxazole | 72° |
| 25 | —NH—CO— (3) | CH₃ | CH₃ | OH | 5-CH₃ | H | isoxazole | 143° |
| 26 | —NH—CO— (3) | CH₃ | CH₃ | OCH₃ | 5-CH₃ | H | isoxazole | 124° |
| 27 | —NH—CO—NH— (3) | CH₃ | CH₃ | H | 5-CH₃ | H | isoxazole | 200° |
| 28 | CH₂NH—CO— (3) | CH₃ | CH₃ | H | 5-CH₃ | H | isoxazole | 99° |
| 29 | —NH—CO— (3) | CH₃ | CH₃ | H | 5-CH₂OH | H | isoxazole | 95° |
| 30 | —NH—CO— (3) | CH₃ | CH₃ | OH | 5-CH₂OH | H | isoxazole | 138° |
| 31 | —NH—CO— (3) | CH₃ | CH₃ | Br | 5-CH₃ | H | isoxazole | 115° |

We claim:

1. A heterocyclic compound of the formula

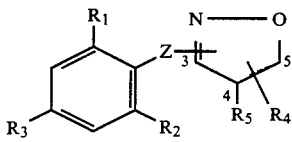

in which the dotted line represents the possibility of a double-bond,

R₁ and R₂ is each selected from C₁-C₄ alkyl, phenyl, benzyl, trifluoromethyl and halogen, R₃ is selected from hydrogen, hydroxy, C₁-C₄ alkyl and alkoxy, R₄, at position 3 or position 5, is selected from hydrogen, trifluoromethyl, C₁-C₄ alkoxy, C₁-C₄ alkyl, and C₁-C₄ hydroxyalkyl, R₅ is selected from hydrogen and C₁-C₄ alkyl, or R₄ and R₅ together form tetramethylene, Z, at position 3 or 5 on the heterocycle, is selected from —N(R₆)—CO—, —CH(R₆)—NH—CO, and —NH—CO—CH(R₆)—, in which R₆ is selected from hydrogen or C₁-C₄ alkyl;

provided that, when Z is at position 5, R₄ and R₅ do not simultaneously represent hydrogen.

2. A heterocyclic compound according to claim 1, wherein the heterocycle is an isoxazole.

3. A heterocyclic compound according to claim 1, wherein Z is —N(R₆)—CO— in which R₆ is hydrogen.

4. 3-(2,6-dimethyl phenylcarbamoyl) 5-methyl isoxazole.

5. 5-(2,6-dimethyl phenylcarbamoyl) 3-methyl isoxazole.

6. 3-(2,6-dimethyl phenylcarbamoyl) 5-hydroxymethyl isoxazole.

7. 3-(2,6-dimethyl phenylcarbamoyl) isoxazole.

8. 3-(2,4,6-trimethyl phenylcarbamoyl) 5-methyl isoxazole.

9. 3-(2-methyl 6-isopropyl phenylcarbamoyl) 5-methyl isoxazole.

10. 3(2-chloro 6-methyl phenylcarbomoyl) 5-methyl isoxazole.

11. 3-(2,6-dimethyl phenylcarbamoyl) 5-methyl isoxazoline.

12. A heterocyclic compound of the formula

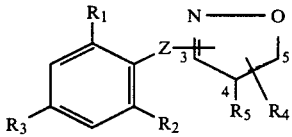

in which the dotted line represents the possibility of a doublebond,

R₁ and R₂ is each selected from C₁-C₄ alkyl, phenyl, benzyl, trifluoromethyl and halogen, R₃ is selected from hydrogen, hydroxy, C₁-C₄ alkyl and alkoxy, R₄, at position 3 or position 5, is selected from hydrogen, trifluoromethyl, C₁-C₄ alkoxy C₁-C₄ alkyl, and C₁-C₄ hydroxyalkyl, R₅ is selected from hydrogen and C₁-C₄ alkyl, or R₄ and R₅ together form tetramethylene, Z, at position 3 or 5 on the heterocycle, is —N(R$_6$)—CO—, in which R$_6$ is selected from hydrogen or C$_1$-C$_4$ alkyl;

provided that, when Z is at position 5, R$_4$ and R$_5$ do not simultaneously represent hydrogen.

13. A heterocyclic compound according to claim 12, wherein the heterocycle is an isoxazole.

14. A heterocyclic compound according to claim 12, wherein Z is —N(R$_6$)—CO— in which R$_6$ is hydrogen.

15. An anticonvulsant composition, comprising as active ingredient an amount effective as an anticonvulsant of a compound according to claim 1 and a pharmaceutically acceptable carrier.

16. A anticonvulsant composition according to claim 15, wherein the unit-dose is between 10 and 100 mg.

17. A method for treating epilepsy in a patient wherein a therapeutically effective amount of a compound of claim 1 is administered to said patient.

* * * * *